United States Patent
Arumugam

(12) 
(10) Patent No.: US 11,946,896 B1
(45) Date of Patent: Apr. 2, 2024

(54) ELECTROCHEMICAL MICRO-SENSOR FOR GABA DETECTION

(71) Applicant: Louisiana Tech Research Corporation, Ruston, LA (US)

(72) Inventor: Prabhu Arumugam, Ruston, LA (US)

(73) Assignee: Louisiana Tech Research Corporation, Ruston, LA (US)

(*) Notice: Subject to any disclaimer, the term of this patent is extended or adjusted under 35 U.S.C. 154(b) by 1064 days.

(21) Appl. No.: 16/810,459

(22) Filed: Mar. 5, 2020

Related U.S. Application Data

(60) Provisional application No. 62/814,581, filed on Mar. 6, 2019.

(51) Int. Cl.
*G01N 27/327* (2006.01)
*G01N 33/94* (2006.01)

(52) U.S. Cl.
CPC ..... *G01N 27/3275* (2013.01); *G01N 33/9426* (2013.01)

(58) Field of Classification Search
CPC ...... G01N 27/48; G01N 27/26; G01N 27/327; G01N 27/3275; G01N 27/10; G01N 27/06; G01N 33/9426; C12Q 1/00; C12Q 1/02; C12Q 1/006; C12Q 1/34; C12Q 1/54; A61B 2562/12
See application file for complete search history.

(56) References Cited

U.S. PATENT DOCUMENTS

| | | | | |
|---|---|---|---|---|
| 2013/0296664 | A1* | 11/2013 | Frey | A61B 5/14532 29/846 |
| 2014/0005492 | A1* | 1/2014 | Harttig | A61B 5/6849 156/60 |
| 2017/0079568 | A1* | 3/2017 | Gerhardt | A61B 5/6868 |

OTHER PUBLICATIONS

Hossain et al., Frontiers in Neuroscience, 2018, 1-13 (Year: 2018).*

* cited by examiner

*Primary Examiner* — Gurpreet Kaur
(74) *Attorney, Agent, or Firm* — Jones Walker LLP

(57) ABSTRACT

A GABA detecting probe having a probe body with both a glutamate (Glu) micro-sensor and a GABA micro-sensor positioned on the probe body. The Glu micro-sensor and the GABA micro-sensor include electrodes having a surface modification with (i) GOx and a binding matrix, and (ii) GABASE, GOx, and the binding matrix, respectively. The sensors are positioned no further apart than 250 um and includes a sentinel site located on the probe body.

20 Claims, 11 Drawing Sheets

GABA + α-ketoglutarate ⟶ SSA + Glu$_{GABA}$ (reaction 1)

Glu + H$_2$O + O$_2$ ⟶ α-ketoglutarate + NH$_3$ + H$_2$O$_{2(g)}$ (reaction 2)

Glu$_{GABA}$ + H$_2$O + O$_2$ ⟶ α-ketoglutarate + NH$_3$ + H$_2$O$_{2(GABA)}$ (reaction 4)

SSA + H$_2$O ⟶ SA + 2H$^+$ + 2e$^-$ (reaction 5)

[GABA] = I$_{GABA}$ = ΔI = H$_2$O$_{2(Site\,2)}$ − H$_2$O$_{2(Site\,1)}$ (Scheme 1)

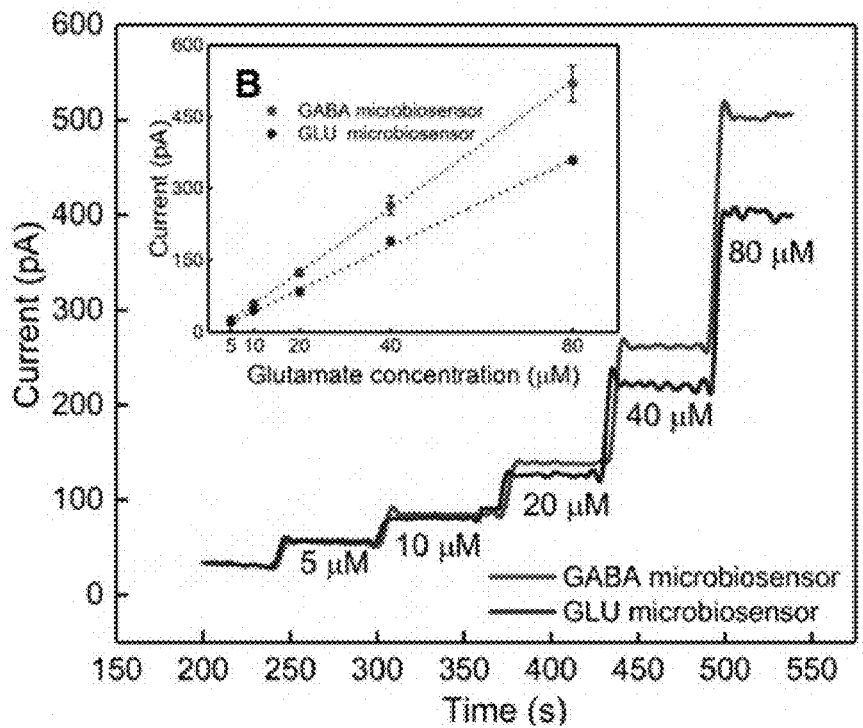
FIGURE 8A, B
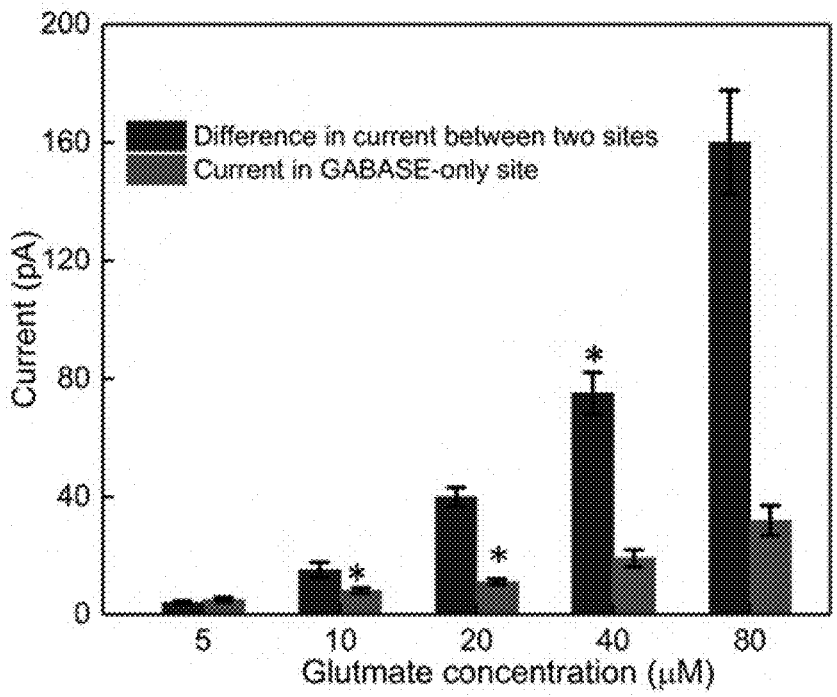
FIGURE 8C

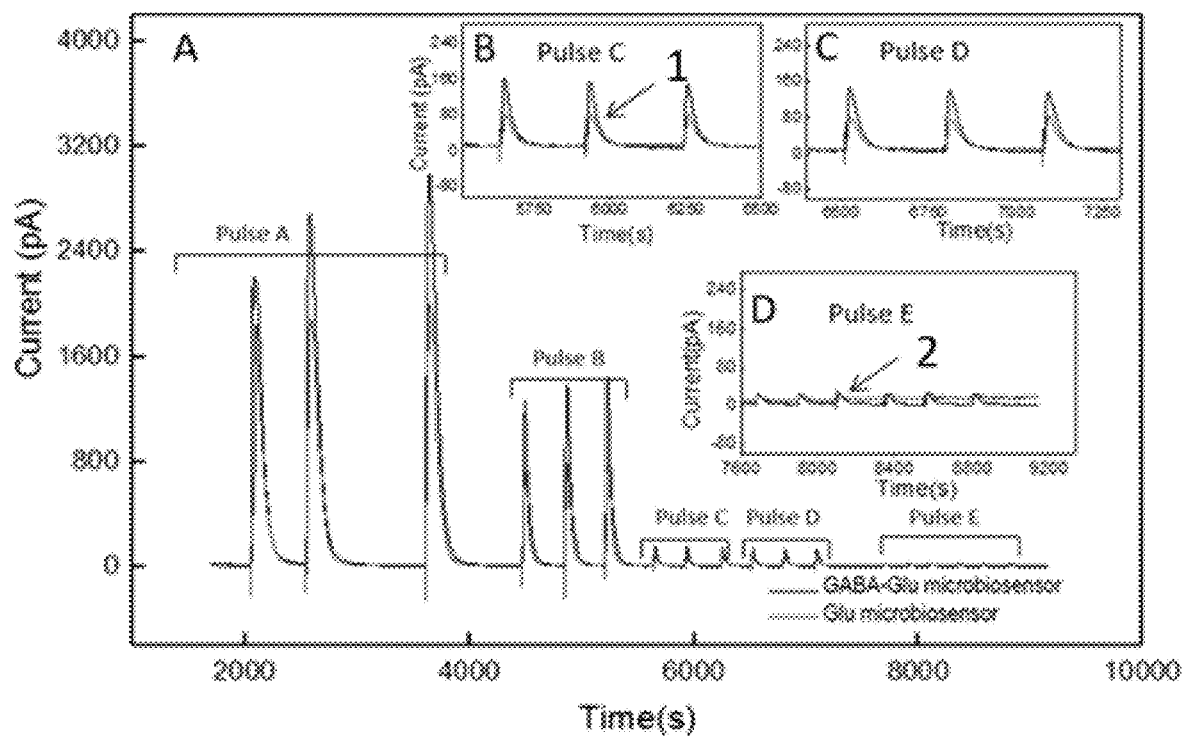
FIGURES 11A, B, C, D
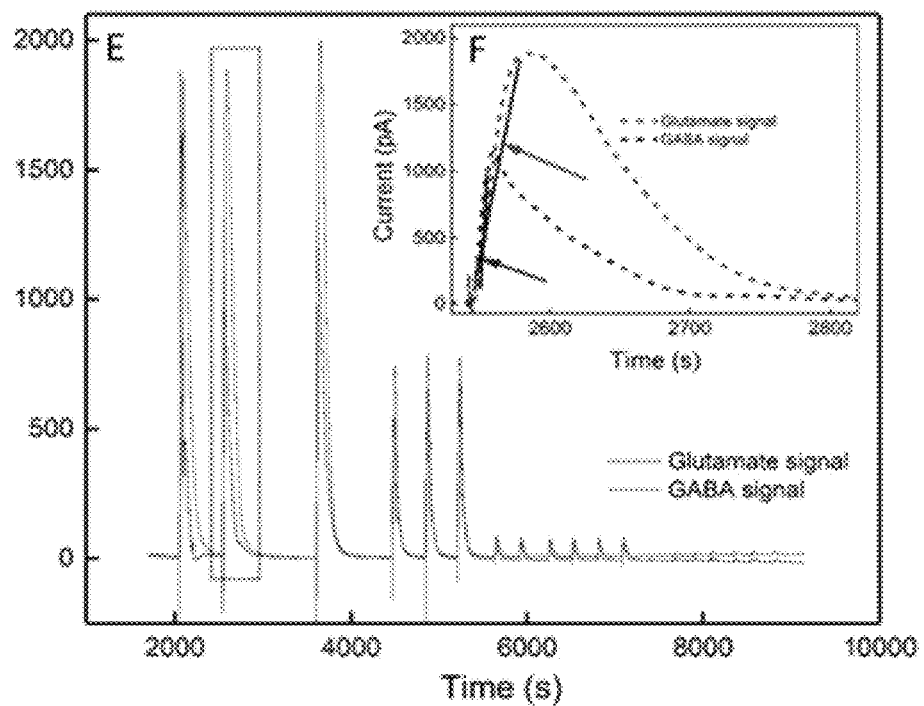
FIGURES 11E, F

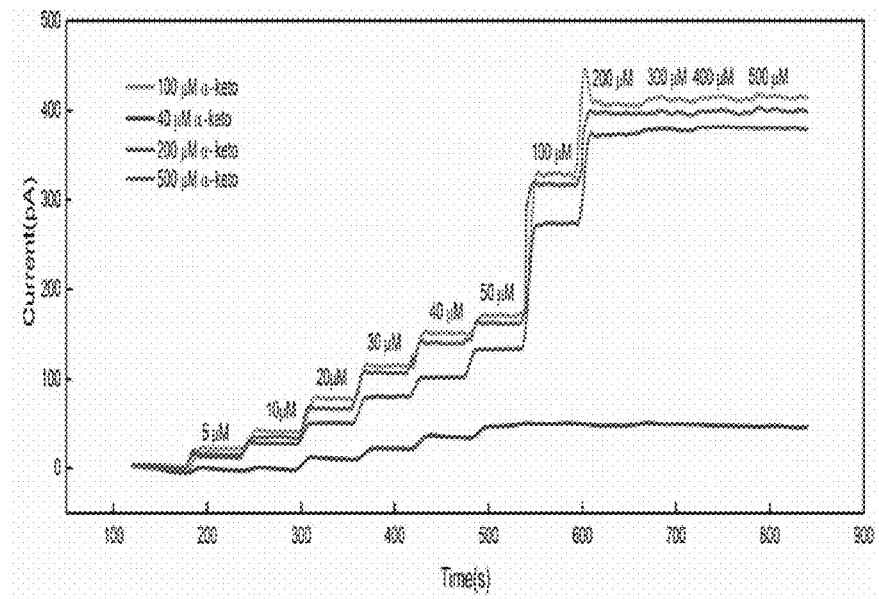
FIGURE 13
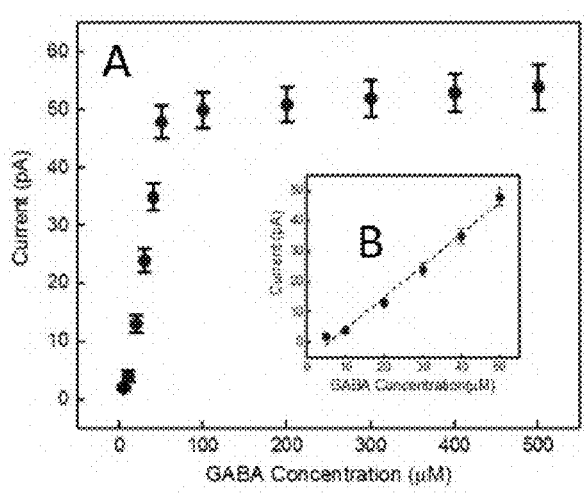 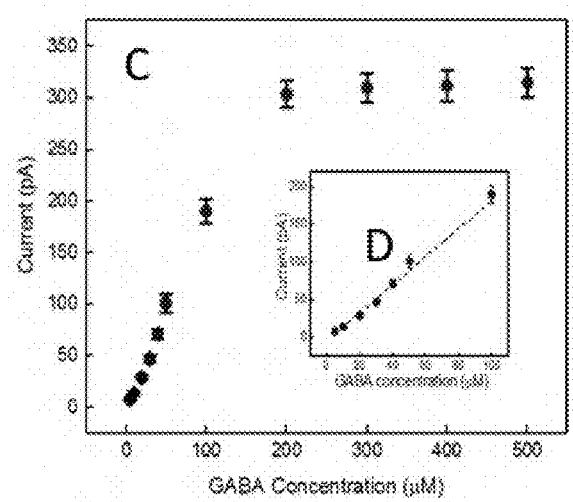
FIGURE 14A, BFIGURE 14C, D

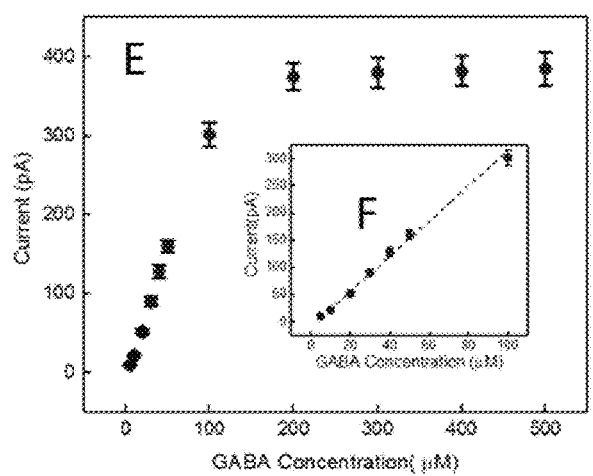 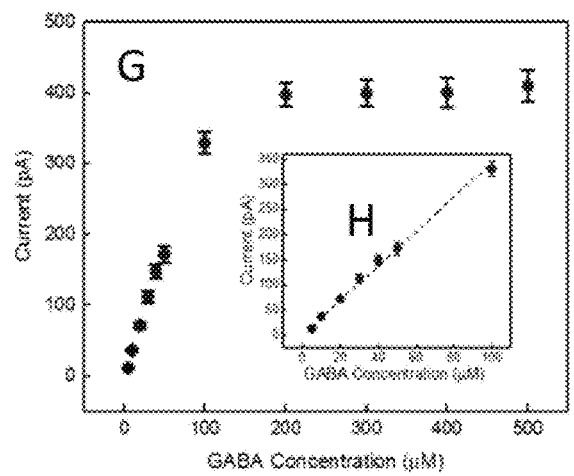
FIGURE 14E, F  FIGURE 14G, H

ELECTROCHEMICAL MICRO-SENSOR FOR GABA DETECTION

CROSS-REFERENCE TO RELATED APPLICATION

This application claims the benefit under 35 USC § 119(e) of U.S. Provisional Application Ser. No. 62/814,581 filed Mar. 6, 2019, which is incorporated by reference herein in its entirety.

STATEMENT REGARDING FEDERALLY SPONSORED RESEARCH OR DEVELOPMENT

This invention was made with government support under NSF Grant No. 1632891. The government has certain rights in the invention.

BACKGROUND

Gamma-aminobutyric acid (GABA) is a major inhibitory neurotransmitter that is essential for normal brain function. It is involved in multiple neuronal activities, including plasticity, information processing and network synchronization. Abnormal GABA levels result in severe brain disorders and therefore GABA has been the target of a wide range of drug therapeutics. GABA being non-electroactive is challenging to detect in real-time. To date, GABA is detected mainly via microdialysis with a high-performance liquid chromatography system that employs electrochemical and spectroscopic methodology. However, these systems are bulky and unsuitable for real-time continuous monitoring. As opposed to microdialysis, biosensors are easy to miniaturize and are highly suitable for in vivo studies. Typically, such biosensors selectively oxidize GABA into a secondary electroactive product (usually hydrogen peroxide, $H_2O_2$) in the presence of enzymes, which is then detected by amperometry. Unfortunately, this method requires a rather cumbersome process with prereactors and relies on externally applied reagents. Biosensors operating without these disadvantages would be a significant improvement in the art.

SUMMARY OF SELECTED EMBODIMENTS OF THE INVENTION

One embodiment of the present invention is a GABA detecting probe. The probe has a probe body with both a glutamate (Glu) micro-sensor and a GABA micro-sensor positioned on the probe body. The Glu micro-sensor and the GABA micro-sensor include electrodes having a surface modification with (i) GOx and a binding matrix, and (ii) GABASE, GOx, and the binding matrix, respectively. This embodiment positions the sensors no further apart than 250 um and includes a sentinel site located on the probe body.

Another embodiment of the present invention is a method of detecting GABA in a brain cell mass. The method includes inserting the above described probe body into the brain cell mass, and then receiving at a potentiostat electrical signals from connecting leads on the probe and determining an electro-potential difference between the GABA micro-sensor and Glu micro-sensor.

BRIEF DESCRIPTION OF THE DRAWINGS

FIGS. 8A to 8C are charts illustrating GABA probe calibration in different concentrations of Glu.

FIGS. 11A to 11F are charts illustrating ex vivo recording of stimulated release of Glu and GABA in rat hippocampal slice preparation.

FIG. 13 is a chart illustrating the calibration of GABA at different concentrations of α-ketoglutarate.

FIGS. 14A to 14H are charts illustrating the current response of GABA at different concentrations of α-ketoglutarate.

DETAILED DESCRIPTION OF SELECTED EMBODIMENTS

Figure 1:
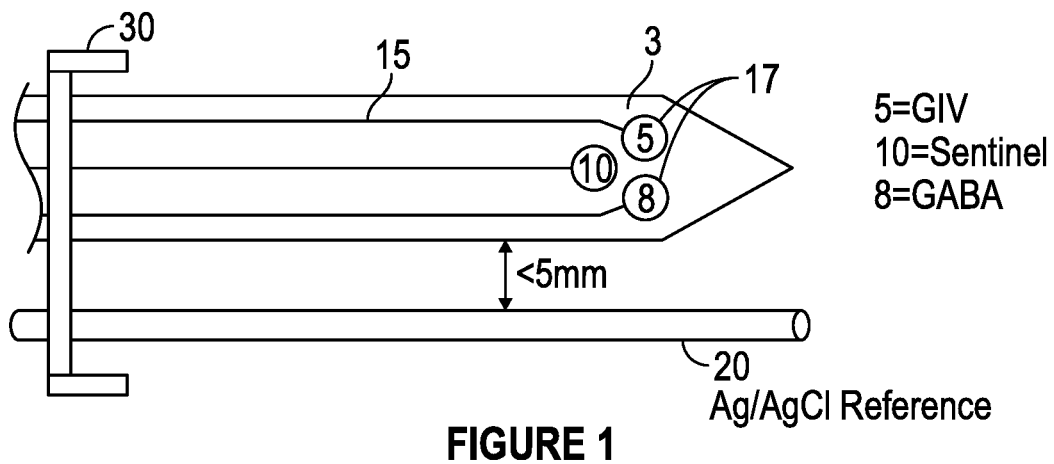
FIG. 1 illustrates conceptually one embodiment of the micro-sensor of the present invention.

One embodiment of the present invention is a GABA detecting probe as suggested in FIG. 1. In general, the GABA detecting probe 1 includes a probe body 3 which has a glutamate (Glu) micro-sensor 5 (also sometimes referred to as "microbiosensor") located on the probe body and a GABA micro-sensor 8 located on the probe body 3. Both the Glu micro-sensor 5 and the GABA micro-sensor 8 will be formed by a metal electrode 17 (typically formed of platinum) which has a binding matrix and enzyme mixture adhering to the electrode. Although platinum is one preferred metal for the electrodes, other conductive metals and alloys could form the electrodes. The electrodes typically have surface area of any size less than 35,000 $um^2$, and more preferably between 500 and 20,000 $um^2$. Each electrode 17 will have a connecting lead 15 which attaches to the electrode and extends along the probe body to a point where the connecting leads can attach to a monitoring device (e.g., a potentiostat). In one preferred embodiment, the binding matrix is a bovine serum albumin (BSA) and glutaraldehyde, which is initially coated onto the electrodes. However, the binding matrix may be any other compound which tends to modify the enzymes to have a surface charge sufficient to allow them to adhere to the metal electrodes, including poly(ethylene glycol) diglycidyl ether (PEGDE), Dimethyl adipimidate (DMA), or Dimethyl suberimidate (DMS).

In one embodiment, the Glu micro-sensor is formed by coating onto the electrode (associated with the Glu micro-sensor) a mixture of glutamate oxidase (GOx) and the binding matrix. To form the GABA micro-sensor, a mixture of both GOx and GABASE (together with the binding matrix) is coated onto the electrode forming the micro-sensor. GABASE is one enzyme used for the enzymatic analysis of GABA. One embodiment of GABASE described herein consists of two enzymes, γ-aminobutyrate aminotransferase (GABA-T) and succinic semialdehyde dehydrogenase (SSDH) obtained from *Pseudomonas fluorescens*. However, the term GABASE is intended to denote any enzyme that selectivity digests or oxidizes GABA. The above example of GABASE from *Pseudomonas fluorescens* may be obtained from Sigma Aldrich (Product No is G7509-10UN). Typically, enough of the enzymes are formed on the electrodes in order to provide at least 0.02 units of activity (or alternatively, an amount which provides anywhere from at least 0.02 to at least 0.2 units of activity). In one example, the enzyme-binding matrix mixture for the Glu micro-sensor was 0.1 U/µL GOx+0.8% BSA+0.1% glutaraldehyde; and for the GABA micro-sensor was 0.1 U/µL GOx+0.1 U/µL GABASE+0.8% BSA+0.1% glutaraldehyde. However, in other examples, the enzyme-binding matrix mixture for the Glu micro-sensor could vary in the range of: 0.05 to 0.5 U/µL GOx+0.5% to 1.5% BSA+0.05% to 0.5% glutaraldehyde, while the enzyme-binding matrix mixture for the GABA micro-sensor could vary in the range of: 0.05 to 0.5 U/µL GOx+0.05 to 0.5 U/µL GABASE+0.5% to 1.5% BSA+0.05% to 0.5% Glutaraldehyde.

In addition to the Glu micro-sensor and a GABA micro-sensor, a sentinel site (micro-sensor) 10 is also located on the probe body. The sentinel site 10 includes at least one Pt electrode having similar mass of the binding matrix formed on it, but with no enzymes (e.g., GOx or GABASE). Different techniques may be used to apply the enzyme-binding matrix mixture to the electrodes. Non-limiting examples include dip-coating, micro-spot coating/casting, and electro-chemical deposition through electric potential/voltage cycling.

In the embodiments described herein, the GABA and Glu micro-sensors are positioned no further than 250 um apart on the probe body, and more preferably, no further than 100 um apart. The sentinel site is also typically positioned less than 250 um (and more preferably less than 100 um) from the Glu and GABA micro-sensors.

Figure 2A:
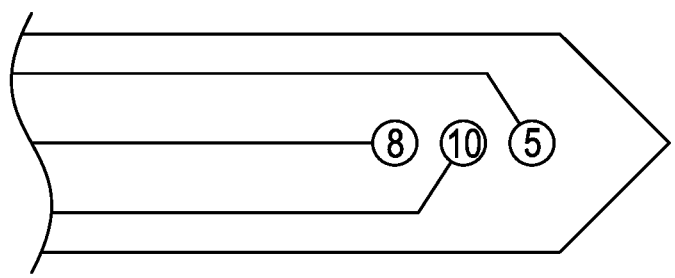
FIGS. 2A to 2C illustrate alternate micro-sensor arrangements on a probe body.
Figure 2B:
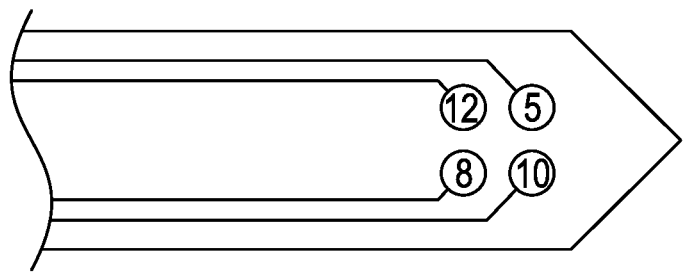
Figure 2C:
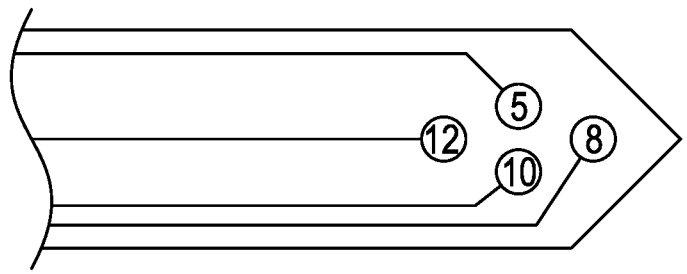

As suggested in FIGS. 2A to 2C, different arrangements of the micro-sensors on the probe body may be employed. In FIG. 2A, the Glu micro-sensor 5, the sentinel site 10, and the GABA micro-sensor 8 are shown inline along the long axis of the probe body 3. In FIG. 2B, the micro-sensor electrodes are shown in a square configuration. In addition to the Glu, the sentinel, and the GABA micro-sensors, there is shown a redundant micro-sensor 12, which could be another Glu or GABA or sentinel micro-sensor. FIG. 2C shows the same number of micro-sensors as in FIG. 2B, but in a diamond configuration.

In a typical embodiment suggested in FIG. 1, some type of reference electrode 20 is used to measure the potential of the electrodes at the GABA micro-sensor, the Glu micro-sensor, and the sentinel site (also sometimes referred to as the "working electrodes"). The reference electrode is positioned relative to the probe body (whether patterned on the probe body or not) in order to form the "electrochemical cell" in relation to the working electrodes. In one embodiment, the reference electrode is an Ag/AgCl wire electrode, but could be other materials, including a saturated calomel electrode (SCE). Normally, the reference electrode 20 will be positioned less than about 5 mm from the working electrodes, but can be much closer depending on the biological system under study.

In operation, the connecting leads 15 from the various electrodes will be connected to some type of device for detecting electro-potential differences (e.g., differences in voltage, current, resistivity, etc.). In one embodiment, this device is a potentiostat receiving the connecting leads and configured to determine an electro-potential difference among the GABA and Glu micro-sensors and the sentinel site. In the illustrated embodiments, the electro-potential difference is a difference in current. Naturally, many devices other than a potentiostat can be employed as long as the device is capable of applying a potential and measuring a corresponding current.

Figures 3, 4:
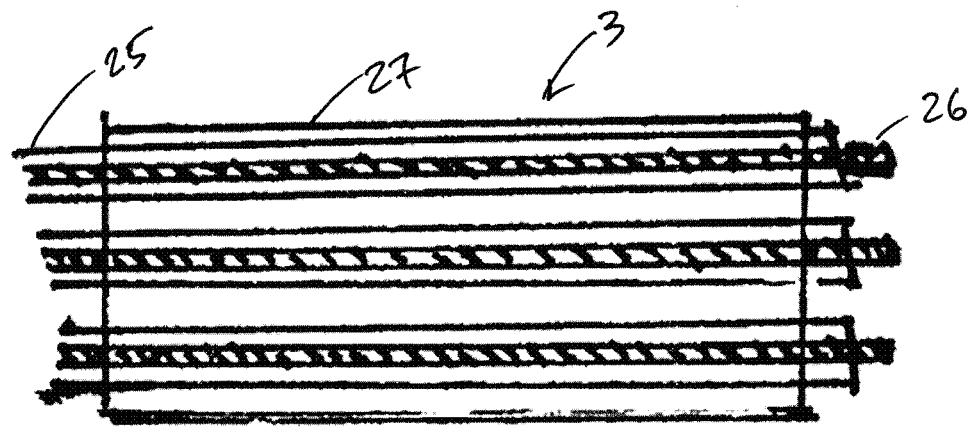
FIG. 3 illustrates various reactions taking place around the micro-sensors.
FIG. 4 illustrates a probe body formed of micro-wires.

FIG. 3 illustrates the reactions taking place during operation of the GABA probe. The Glu micro-sensor 5 modified with GOx only allows reaction 2 to occur and with the GABA micro-sensor 8 modified with GOx and GABASE allows reactions 1, 2 and 4 to occur. By simultaneously measuring and subtracting the oxidation currents of $H_2O_2$ generated from the two micro-sensors, i.e. $IH_2O_2$ from $H_2O_{2(E)}$ at Glu micro-sensor 5 (henceforth called $IH_2O_{2(site\ 1)}$) and $IH_2O_2$ from $H_2O_{2(E)}$ and $H_2O_{2(GABA)}$ at GABA micro-sensor 8 (henceforth called $IH_2O_{2(site\ 2)}$), GABA ($I_{GABA}=\Delta I=IH_2O_{2(site\ 2)}-IH_2O_{2(site\ 1)}$) can be detected continuously in real time (Scheme 1, FIG. 3) without adding α-ketoglutarate externally. This is possible because α-ketoglutarate generated in reaction 2 is used in reaction 1. Scheme 1 can be readily implemented ex vivo and in vivo because the ubiquitous presence of $Glu_E$ allows in situ generation of α-ketoglutarate, and thus reaction 1 to occur continuously. The SSA generated in reaction 1 is converted to SA when periplasmatic aldehyde reductase is present on the electrode surface (reaction 5, FIG. 3). See Badalyan, A., Dierich, M., Stiba, K., Schwuchow, V., Leimkuhler, S., and Wollenberger, U. (2014). *Electrical wiring of the aldehyde oxidoreductase PaoABC with a polymer containing osmium redox centers: Biosensors for benzaldehyde and GABA*. Biosensors 4, 403-421. doi:10.3390/bios4040403, which is incorporated by reference herein.

Those skilled in the art will recognize that the sentinel site controls for the electro-potential influence deriving from the binding matrix and the current generated at this site is solely from the interferents. Since the sentinel site electrode has only the binding matrix formed on it, $IH_2O_{2(site\ 2)}$ and $IH_2O_{2(site\ 1)}$ should be considered as the oxidation current at these two sites subtracted from the oxidation current at the sentinel electrode, respectively, in order to obtain the currents solely from the Glu and GABA and to remove any current signal originating from the interferents.

The probe body can be constructed in many different ways. In one embodiment, the probe body is a generally elongated section of rigid, substantially non-conducting or insulating material such as an un-doped silicon, a ceramic, or polymers like polyimide, PMMA, PDMS, SU8 etc. In certain examples, the probe body is less than 5 mm in width and less than 15 mm in length, and the electrodes and leads may be formed (e.g., of platinum) on the probe body by any conventional or future developed process, including as examples, a physical vapor deposition technique, e.g., sputter depositing, thermal or electron beam depositing, or an electro-chemical deposition or plating technique. Multiple sets or pairs of micro-sensors could be positioned along the body of the probe. For example, a first pair of a GABA micro-sensor and a Glu micro-sensor could be positioned near the terminal end of the probe body. 1 mm further along the probe body, a second pair of GABA and Glu micro-sensors could be formed, and then a third pair of GABA and Glu micro-sensors still further along the probe body. Preferably, there is one sentinel site as a baseline for multiple pairs, and there may also be redundant sentinel sites which improve statistical robustness. In this manner, the probe inserted into tissue, could detect GABA presence and/or concentrations levels at different depths or layers within the tissue. FIG. 1 suggests how one end of the probe body 3 may be formed with a pointed tip to aid with insertion into the tissue.

In another embodiment suggested in FIG. 4, the probe body may formed by a plurality of insulated micro-wires 25 which are bound together. Generally, the micro-wires can be any wire under a few millimeters in diameter. As a specific example, such a micro-wire would include 125 um platinum wire having a polymer insulation coating about 50 um thick. Three such wires could be bound together (e.g., by shrink wrap tubing 27). Prior to binding together, the insulation could be removed from the terminal 100 um tip 26 of the wires and the enzyme/binding matrix applied to each exposed micro-wire tip 26. For example, the binding matrix and GOx mixture is applied to a first micro-wire tip in order to form the Glu micro-sensor; the binding matrix, GABASE, and GOx mixture is applied to a second micro-wire tip to form the GABA micro-sensor; and the binding matrix alone is applied to a third micro-wire tip to form the sentinel site. When the micro-wires are bound together with the tips approximately aligned, the insulation layer will tend to space the micro-sensors about 100 um apart. Those skilled in the art will see still further ways the probe body may be created in keeping with the concepts disclosed herein.

Because one primary function of the above described probe is to detect neurotransmitter compounds such as GABA, in use the probe will often be placed in a brain cell mass of a mammal, including but not limited to human brain cell masses. Examples of such brain cell masses may include (i) a culture of mammal brain cells, (ii) a tissue slice of a mammal brain, or (iii) the mammal brain itself when employed in an in vivo application. In one example of an in vivo application, a plastic cannula is positioned in the brain of the mammal being monitored. As suggested in FIG. 1, the rear portion of probe body 3 may be attached to a cap 30, with the connector leads 15 extending through cap 30. Similarly, reference electrode 20 is connected to and extends through cap 30. Cap 30 is configured such that it snaps onto or threads onto the end portion of the cannula extending from the mammal brain. The length of probe body 3 and reference electrode 20 are configured such that when cap 30 engages the cannula, the portion of the probe carrying the micro-sensors come into contact with the brain tissue to be tested/monitored.

As suggested above, the reference electrode may be positioned at different locations relative to the probe body as long as the reference electrode can for the "electrochemical cell" in relation to the working electrodes. In most preferred embodiments, a potential will be maintained between the reference electrode and the working electrodes of between about 0.6 and about 0.8 volts. This range of voltage is generally preferred when attempting to detect $H_2O_2$.

Those skilled in the art will see many advantages arising from the above described GABA probe. For example, the probe allows for a plurality of individually electrically addressable Pt microelectrodes that can easily be multiplexed to simultaneously measure other important neurochemicals, such as Glu, DA, adenosine and HT-5, through suitable surface modifications, which is not possible with other commonly available electrodes for chemical sensing, e.g. carbon fiber microelectrodes. Additionally, the GABA and Glu micro-sensors can be placed in close proximity to provide precise measurements of local GABA level changes, thereby detecting GABA in real-time without adding reagents (i.e. truly self-contained system). The location of multiple pairs of micro-sensors along the long shank of the probe body allows GABA sensing at multiple depths in the brain; and also allows simultaneous sensing of neurochemicals and field potentials for multimodal recordings, which is not possible with the current neurochemical technologies.

EXPERIMENTAL EXAMPLE

Materials And Methods
Chemicals

Figure 5:
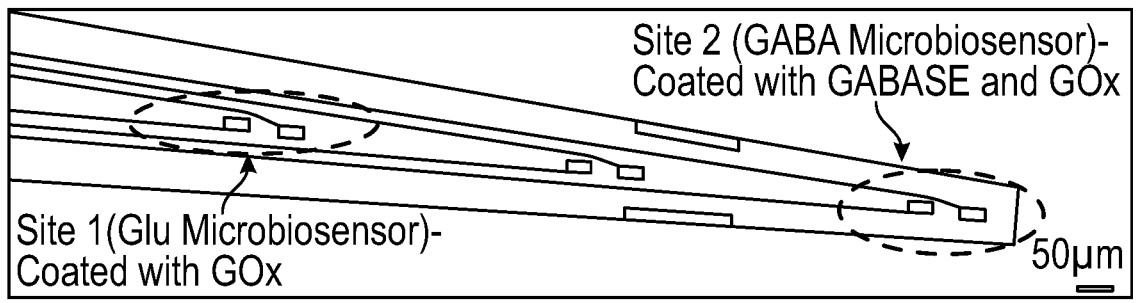
FIG. 5 illustrates one commercially available probe body used in the experimental example.

Phosphate buffered saline (PBS), bovine serum albumin (BSA), glutaraldehyde, GABA, GABASE from *Pseudomonas fluorescens* and α-ketoglutarate disodium salt was purchased from Millipore-Sigma (MO, USA). Glutamate oxidase was purchased from Cosmo Bio USA (CA, USA).
GABA Probe Preparation The platinum (Pt) MEA (8-TRK probe) was purchased from Center for Microelectrode Technology (CenMeT, USA). The MEA consists of eight Pt microelectrodes (50 μm×100 μm, two microelectrodes per site) and the sites are spaced at 1 mm apart. Each site has two closely spaced (100 μm apart) microelectrodes (FIG. 5). Since the in vitro experiments were carried out in a stirred solution in a beaker, it is not expected to see any effect or variability particularly on the Glu signal due to this spatial variation. For ex vivo measurements in brain tissue slices, the two Pt microelectrodes (located in Site 2, as shown in FIG. 5, and spaced 100 m apart) were coated with GOx and GABASE+GOx, respectively.

Enzyme aliquot preparation. The GOx enzyme with the BSA and glutaraldehyde was coated in Site 1 as per Burmeister et al. (Burmeister et al., 2013). For Site 1, the GOx enzyme was mixed in DI water to prepare aliquots of 0.5 U/μL and stored in −80° C. Prior to coating, they were thawed first at 4° C. and then at room temperature. DI water (985 μL) was added to 10 mg BSA in a 1 mL centrifuge tube. After allowing the BSA to dissolve, 5 μL of glutaraldehyde (25% in water) was added to the solution. The solution mixture (1% BSA and 0.125% glutaraldehyde) was kept at room temperature for ~5 min. A 4 μL of the mixture was added to 1 μL of GOx (0.5 U/μL) and centrifuged to form the final enzyme-matrix mixture of 0.1 U/μL GOx/0.8% BSA/ 0.1% glutaraldehyde. Similarly, for Site 2, DI water (986.7 μL) was added to 13.33 mg BSA in a 1 mL centrifuge tube. After allowing the BSA to dissolve, 6.67 μL of glutaraldehyde (25% in water) was added to the solution. The solution mixture (1.33% BSA and 0.166% glutaraldehyde) was kept at room temperature for ~5 min. Next, 3 μL of the mixture was added to 1 μL of GOx (0.5 U/μL) and 1 μL GABASE (0.5 U/μL) and centrifuged to form the final enzyme-matrix mixture of 0.1 U/μL GOx/0.1 U/μL GABASE/0.8% BSA/ 0.1% glutaraldehyde. For the GABASE-only site, the procedure used for Site 1 was followed except that GABASE instead of GOx was used.

Figure 6A:
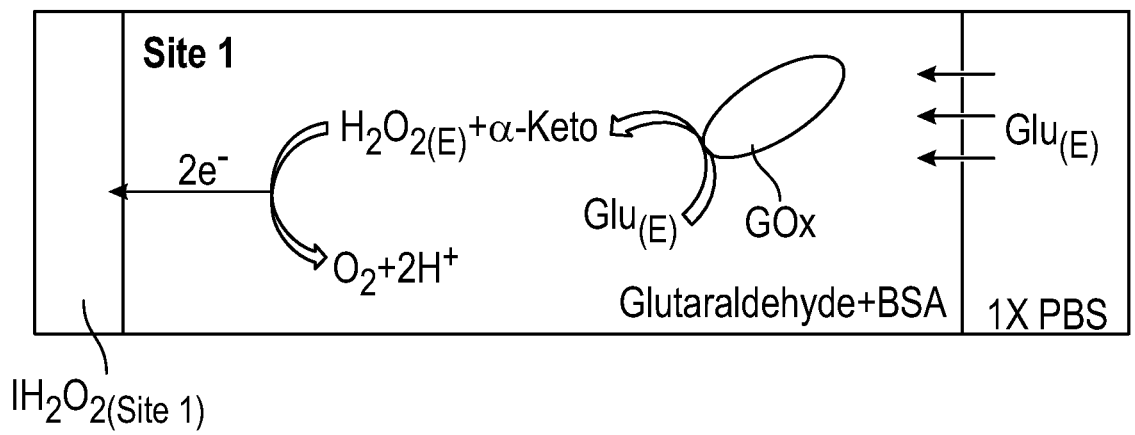
FIGS. 6A and 6B illustrate reaction pathways of one embodiment.
Figure 6B:
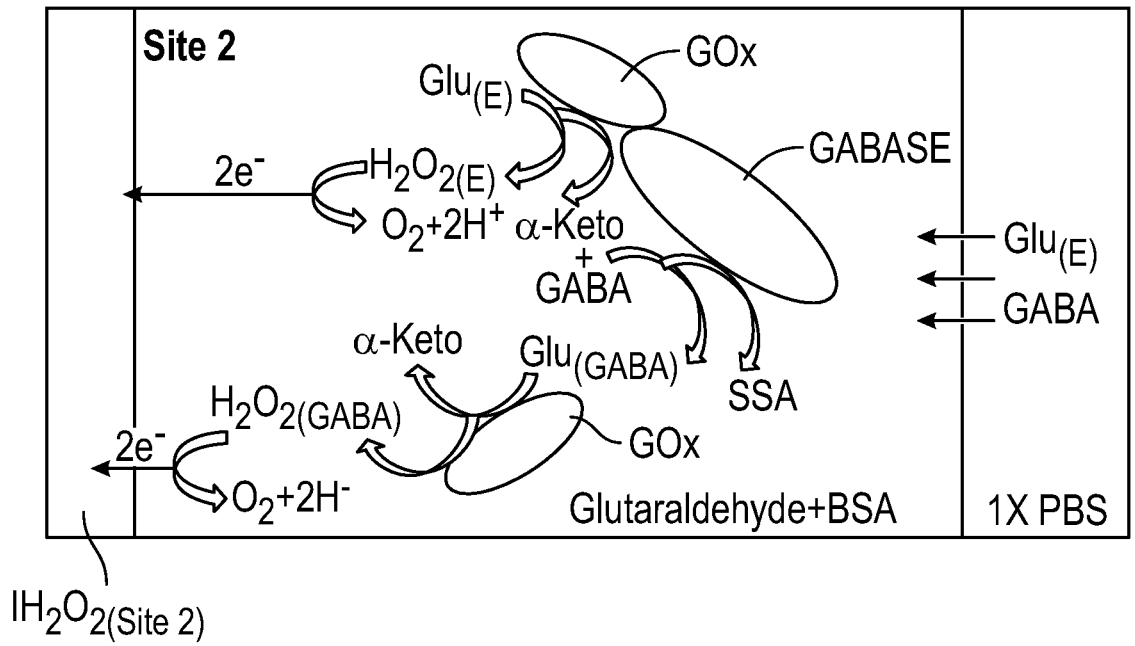

Enzyme coating procedure: Under a Nikon stereomicroscope (Model, SMZ18), three drops (0.05 L/drop) of the respective enzyme-matrix mixture was applied manually at each site using a microsyringe (Hamilton®, Model 701 N). Then the probe was stored for 48 h in an aluminum foil covered storage container with no exposure to light prior to use. FIG. 6 shows the cross-sectional schematic of the GABA probe with reaction pathways in Sites 1 and 2.
Electrochemical Measurements For amperometry measurements, a multichannel FAST-16mkIII® potentiostat (Quanteon, LLC, Nicholasville, KY) in a 2-electrode setup was used with an Ag/AgCl electrode as the reference electrode. The applied potential was set at +0.7 V for $H_2O_2$ detection. The experiment was carried out in a 40 mL buffer solution. The analytes were introduced into the solution using a syringe pump (KD Scientific, Legato® 100 syringe pump) to obtain the desired concentrations (M). The solution was continuously stirred at 200 rpm and maintained at 37° C. All measurements were repeated 6 times (n=6). The Fast Analysis® software provided by Quanteon was used for data analysis. Sensitivity was defined as the change in current for each unit of analyte addition. Sensitivity was calculated from the slope (pA/μM) of the calibration curves. Then the slope was converted into nA $\mu M^{-1}$ $cm^{-2}$ by dividing it by the Pt microelectrode area ($5 \times 10^{-5}$ $cm^2$). The limit of detection (LOD) was calculated by dividing (3 times the standard deviation of 10 points from the baseline) by the least squares slope, which is based on the FAST 2014 software manual provided by Quanteon. The baseline is the signal that was obtained when no electroactive analyte was present in the solution. Two-tailed Students t-test was performed (n=6) at two different confidence intervals. They are 99.99% (p<0.0001) and 95% (p<0.05). The values lie within p<0.0001 unless otherwise stated. The value which lies within p<0.05 are represented with (*) in the bar charts and tables. One-way ANOVA was performed (n=6) with significance defined as p<0.05 to verify if sensor-to sensor variation (in the same site) is significant. Error value is shown as mean±SEM.

Recording GABA and Glutamate in Brain Tissue

Animal care and use: Male Sprague Dawley rats were housed on a 12 h on-12 h off cycle with food and water provided ad libitum, according to a Louisiana Tech University IACUC protocol, the Guide for the Care and Use of Laboratory Animals and the AVMA Guidelines on Euthanasia.

Hippocampal slice preparation: Hippocampal slices were prepared from an adult Sprague Dawley rat that was anesthetized using 5% isoflurane gas prior to decapitation and rapid removal of the brain. The brain was immediately placed into ice cold artificial cerebral spinal fluid (aCSF) containing (in mM): 135 NaCl, 3 KCl, 16 $NaHCO_3$, 1 $MgCl$, 1.25 $NaH_2PO_4$, 2 $CaCl_2$), and 10 glucose, bubbled with 95% $O_2$/5% $CO_2$ (carbogen) (Song et al., 2005). The slicing chamber of an OTS-5000 tissue slicer (Electron Microscopy Sciences) was filled with aCSF at 4° C. and then 500-μm thick coronal sections were cut and transferred to a holding chamber filled with aCSF maintained at 35° C. and bubbled with carbogen. Slices and were incubated for at least 60 min prior to recording. Thereafter, one slice was transferred to a liquid-air interface of a BSC1 chamber (Scientific Systems Design, Inc.) with the slice suspended on a nylon net at the liquid-air interface with continuously dripping aCSF (37° C.) bubbled with carbogen. Waste products were removed by continuous suction from the recording chamber.

GABA recording in rat hippocampal slices: The microbiosensors were coated with a size-exclusion polymer (m-phenylenediamine, mPD) to prevent the interferents reaching the microbiosensor surface and to enhance the probe selectivity (Wilson, 2017). The mPD layer was electrochemically deposited (cycling between +0.25 V and −0.75 V, 50 mV/s, 20 min in 10 mM mPD solution). A pair of 160-μm diameter tungsten stimulation electrodes was placed in the Schaffer collateral CA1 pathway within 200 m of the microbiosensor probe sites (Song et al., 2005). An A365 stimulus isolator (World Precision Instruments) was used to deliver 100-μA direct current pulses to the stimulus electrodes; pulse widths were regulated by transistor-transistor logic (TTL) input from an Arduino microcontroller. Current detected at the probe sites was plotted in real time.

Data analysis for ex vivo recordings: Results from ex vivo, hippocampal recordings were analyzed using OriginPro 2017. Measurements are reported as the mean±square error of the mean (SEM). ANOVA was performed for comparisons of means and significance was defined as p<0.05. Rise times ($T_{r10-90}$) were defined as the elapsed time between 10% and 90% from the baseline to the peak current of the stimulation response. The Rise Time Gadget tool in OriginPro 2017 was used to calculate the rise time.

Results And Discussion

Calibration of GABA Probe in the Presence of α-Ketoglutarate

Figure 7A:
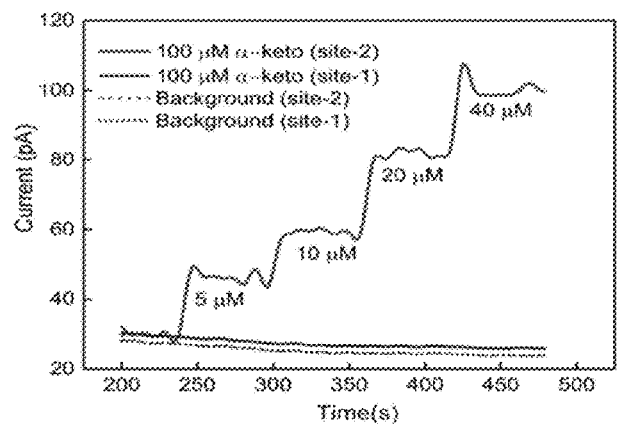
FIGS. 7A to 7D are charts illustrating increasing detection current as a function of increasing GABA concentration.
Figure 7B:
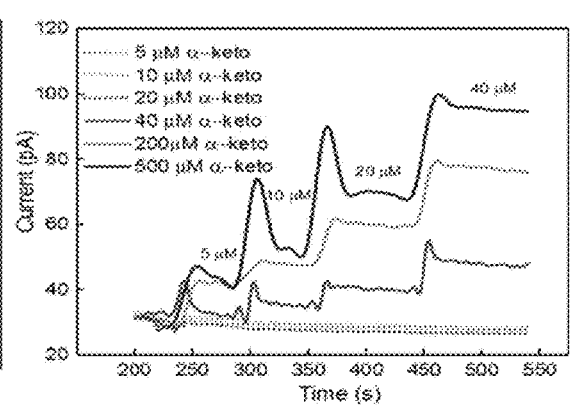
Figure 7C:
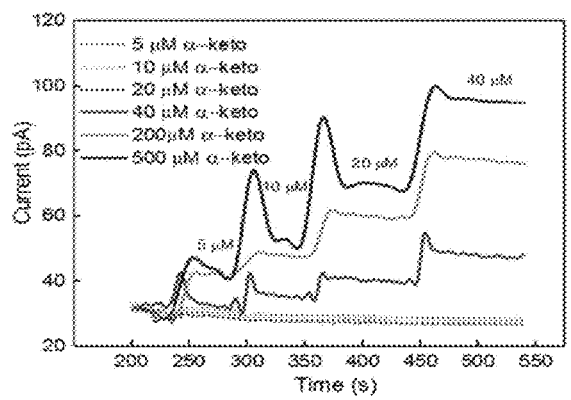
Figure 7D:
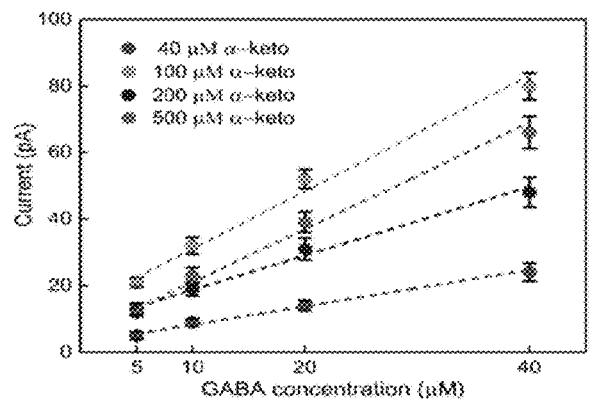

Studies have shown dependence of the GABA current response (pA) on concentration of α-ketoglutarate (Niwa et al., 1998), which is an important molecule in physiological functions, for example in the Krebs cycle (Tretter and Adam-Vizi, 2005). Therefore, first studied was the electrochemical response of the Glu and GABA microbiosensors (Sites 1 and 2) in the presence of different concentrations of α-ketoglutarate (1 μM-500 μM) in the phosphate buffered saline (PBS) solution. FIG. 7A shows the typical AM responses at Sites 1 and 2 in 1×PBS supporting electrolyte (background or control, blue dashed, red dashed curves), and to varying concentrations of GABA (5, 10, 20 and 40 μM) in 100 μM α-ketoglutarate solution prepared in 1×PBS (blue solid, red solid curves). These values of concentration in the micromolar range were chosen because of their relevance to the ones encountered in the brain microenvironment where GABA is typically present (Badalyan et al., 2014). For example, GABA levels are in the range of 20-70 μM in rat brain slices, (Grabauskas, 2004), and up to 1.25 μM/$cm^3$ in the human brain (Ke et al., 2000) as measured by proton magnetic resonance spectroscopy. The AM response was recorded in different concentrations of α-ketoglutarate solution, first by allowing the microbiosensors to stabilize in the solution for up to 240 s, and then injecting GABA at 1 min time intervals to obtain the desirable concentration (FIG. 7B, C). From FIG. 7A, as expected, it was observed that the Glu microbiosensor at Site 1 did not exhibit a response to GABA because of the absence of the GABASE enzyme. Also, there was no enzymatic activity of GOx in converting GABA into Glu and then into $H_2O_2$. This indicates that the GABA conversion is highly selective at Site 2 that has GABASE and not at Site 1. The GABA microbiosensor at Site 2 responded to GABA when the α-ketoglutarate concentration was at least 40 μM (FIG. 7B). A transient spike in the signal was observed during the injection of the solution in the beaker. However, the signal was stabilized a few seconds following the injection of the solution. Sometimes the time to stabilization was a bit longer (e.g. in the case of 40 μM and 500 μM α-ketoglutarate experiments). This might be due to a few bubbles in the micro syringe pump that disturb the solution more in certain experiments than others. The other data points for the same α-ketoglutarate concentrations did not show similar spikes. The highest sensitivity was observed at 100 μM. From FIG. 7D, the sensitivity is 36±2.5 pA $\mu M^{-1}$ $cm^{-2}$ and the LOD is 2±0.12 μM (n=6), which is 10-fold higher than that of similar AM-based microsensors (Niwa et al., 1998). The sensitivities at 40 μM, 200 μM and 500 μM of α-ketoglutarate were 12±1.7, 20±2.4 and 28±2.5 respectively, and the LOD was 7±0.7, 4.0±0.4 and 3±0.24, respectively (Table 1).

TABLE 1

GABA sensitivity and LOD for different α-ketoglutarate concentration.

| α-ketoglutarate concentration (μM) | Sensitivity (nA μM$^{-1}$cm$^{-2}$) | LOD (μM) |
|---|---|---|
| 40 | 12 ± 1.7 | 7 ± 0.7 |
| 100 | 36 ± 2.5 | 2 ± 0.12 |
| 200 | 20 ± 2.4* | 4 ± 0.4 |
| 500 | 28 ± 2.5 | 3 ± 0.24* |

Error value is shown as mean ± SEM.
Two-tailed Students t-test was performed (n = 6, p < 0.0001, *p < 0.05).
One-way ANOVA was performed (n = 6, p < 0.0001) to verify that sensor-to sensor variation (in the same site) is not significant.

This GABA response to α-ketoglutarate concentration is in agreement with previously published literature (Niwa et al., 1998). One possible reason for the decrease of GABA sensitivity at highest α-ketoglutarate concentrations could be due to their scavenging of $H_2O_2$ as suggested by previous studies (Long and Halliwell, 2011; Nath et al., 1995). Another study (Badalyan et al., 2014) showed a similar trend where the GABA sensitivity was highest at 1 mM α-ketoglutarate and then decreased at much higher concentrations. The LOD achieved using the GABA microbiosensor is 2-7 μM, which is lower than the clinically-relevant concentrations (Grabauskas, 2004) and similar to the values achieved by alternative methods (Ke et al., 2000) in the human brain. Sensitivities differ slightly between microelectrodes, which are likely due to variations in the quantity of enzymes that are manually applied to each site. Any potential defects in the surface of the electrodes may also lead to a difference in sensitivity. But this could be remedied by employing an array of GABA and Glu microbiosensors and by applying appropriate statistics (e.g. averaging the current values etc.) in the future. This sensitivity variation can be further minimized by employing micro spotting techniques that are fully automated and dispense very precise volumes of enzyme solutions. Next, to determine the linear range of the calibration plots, generated the plots for 5-500 μM GABA concentrations versus different α-ketoglutarate concentrations were generated. It was observed that the GABA current values saturate, and saturation depends on the α-ketoglutarate concentration (FIGS. 13, 14). For example, for 40 μM α-ketoglutarate, the GABA signal saturation is at 50 μM. Whereas in 100, 200 and 500 μM α-ketoglutarate concentrations, the GABA signal saturation occurs at 100 μM. The trend in sensitivity in the linear range is the same as before. For 100 μM α-ketoglutarate, the GABA sensitivity is highest and becomes lower at other concentrations of α-ketoglutarate.

Calibration of the GABA Probe in the Presence of Glutamate

The GABA probe was calibrated in the presence of a range of concentrations (5-80 μM) of Glu, which mimics the brain microenvironment both in healthy and diseased states. For example, the basal concentration of Glu in the extracellular space is up to 20 μM (Moussawi et al., 2011), while Glu concentrations in cerebrospinal fluid are ~10 μM. During seizures, Glu levels increase 4-fold and GABA levels decrease (Kanamori and Ross, 2011; Medina-Ceja et al., 2015; Rowley et al., 1995a). Glu is a major excitatory neurochemical that is ubiquitously present as L-glutamate in its anionic form (glutamic acid) in the brain environment (henceforth called $Glu_E$) (Moussawi et al., 2011). One of the objectives of this study was to monitor $Glu_E$ as an in-situ source for the generation of α-ketoglutarate, which aids in the continuous real-time GABA monitoring at Site 2, and thus does not rely on the addition of α-ketoglutarate externally. Firstly, the two microbiosensors were calibrated by injecting Glu at various concentrations (5 PM, 10 PM, 20 PM, 40 μM and 80 μM) in 1×PBS buffer solution. FIG. 8A, B shows the response of the two microbiosensors. The GABA microbiosensor (Site 2) consistently exhibited a slightly higher Glu response than that of the Glu microbiosensor (Site 1). The Glu sensitivity of Site 2 and Site 1 are 132 nAμM$^{-1}$ cm$^{-2}$ and 90 nAμM$^{-1}$ cm$^{-2}$, respectively. The difference in the current response from the two microbiosensors increases for higher Glu concentrations (FIG. 8C, blue bars). To further understand this, Site 2 was modified with only GABASE and no GOx. Ideally, there should not be any response from the GABA microbiosensor, however, a small response was observed (FIG. 8C, red bars). This confirms our hypothesis that some non-selective activity of GABASE is due to Glu oxidation. Others have made similar observations where GABASE showed weak enzyme activity towards Glu compared to GOx (Niwa et al., 1998). The large response could also be due to the presence of more enzymes per unit volume (0.2 U/μl) that somehow collectively create more active sites (Arima et al., 2009). To account for this difference in the Glu response, henceforth called the background noise, $I_b$ (shown in FIG. 8C (blue bars)), the $I_b$ was subtracted from the difference in the currents ($I_{GABA}$) at the two sites in order to obtain the final current response to GABA (details discussed later).

Figure 9A:
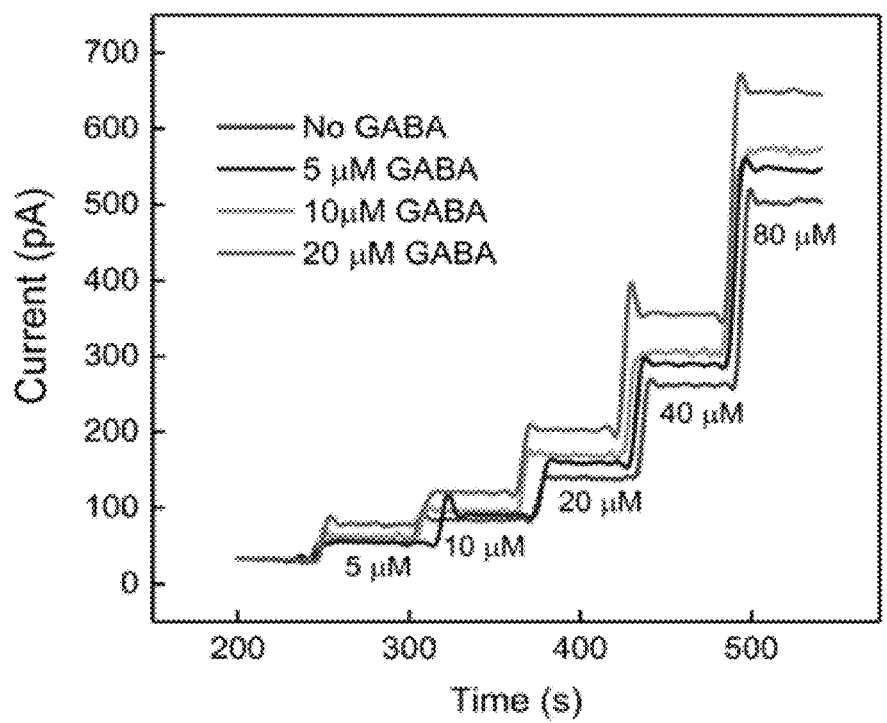
FIGS. 9A and 9B are charts illustrating GABA probe calibration in different concentrations of Glu.
Figure 9B:
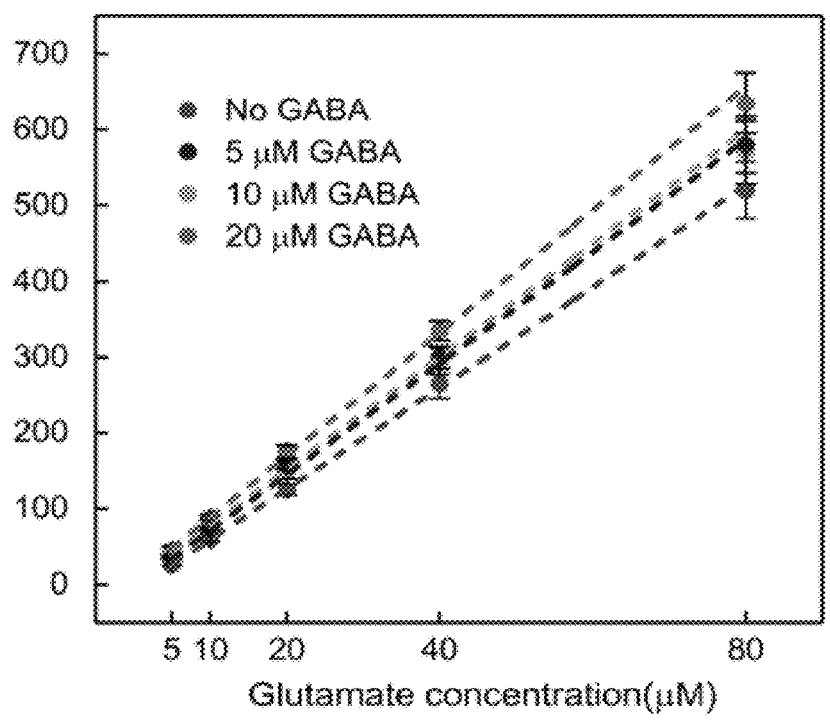

The next calibration step was to test different GABA solutions (0, 5, 10, 20 PM) in 1×PBS buffer and repeat the above Glu calibration (FIG. 9). These experiments were performed without adding α-ketoglutarate externally. At Site 1, $Glu_E$ is oxidized to α-ketoglutarate and $H_2O_{2(E)}$ (reaction 2). This α-ketoglutarate then reacts with GABA at Site 2 and produces $Glu_{GABA}$ (reaction 1) followed by reaction 4, which generates $H_2O_{2(GABA)}$ and more α-ketoglutarate. These reactions and pathways were shown in FIG. 2. At the GABA microbiosensor (Site 2), in the case of no GABA in the solution, the current response ($IH_2O_{2(Site\ 2)}$) is due only to the changing Glu levels in the solution (FIG. 9A, red curve). When GABA is present in the solution, the $IH_2O_{2(Site\ 2)}$ response is from both GABA and Glu oxidation and it was expected to be larger than the response when there was no GABA. Therefore, higher GABA concentrations appear to induce a greater response (FIG. 9A, blue, green, magenta curves) at Site 2 and greater $I_{GABA}$, which is the GABA signal (Scheme 1). FIG. 9B shows the sensitivity of the GABA microbiosensor at different GABA and Glu concentrations. With increasing GABA and Glu concentrations, the sensitivity of the GABA microbiosensor increases and this is because of increased availability of α-ketoglutarate for reaction 1. The sensitivity and the LOD of the two microbiosensors is shown in Table 2.

TABLE 2

Sensitivity and LOD in Site 1 (GOx only) and Site 2 (GOx + GABAse).

| GABA concentration | Sensitivity (nA μM$^{-1}$cm$^{-2}$) | | LOD (μM) | |
|---|---|---|---|---|
| (μM) | Site-1 | Site-2 | Site-1 | Site-2 |
| 0 | 90 ± 5* | 132 ± 13 | 0.27 ± 0.02 | 0.08 ± 0.008 |
| 5 | 104 ± 8 | 146 ± 16 | 0.23 ± 0.01 | 0.08 ± 0.007* |
| 10 | 106 ± 10 | 154 ± 19 | 0.22 ± 0.01 | 0.07 ± 0.008 |
| 20 | 104 ± 12 | 164 ± 21 | 0.23 ± 0.02 | 0.07 ± 0.009 |

Error value is shown as mean ± SEM.
Two-tailed Students t-test was performed (n = 6, p < 0.0001, *p < 0.05).
One-way ANOVA was performed (n = 6, p < 0.0001) to verify that sensor-to sensor variation (in the same site) is not significant.
The GABA sensitivity increased by ~25% at 20 μM GABA concentrations.
The sensitivity reported here is greater than that of the Pt based Glu sensors published in the literature (Tseng et al., 2014)
The LOD is comparable to other Glu sensors (Khan et al., 2011).

Figure 10A:
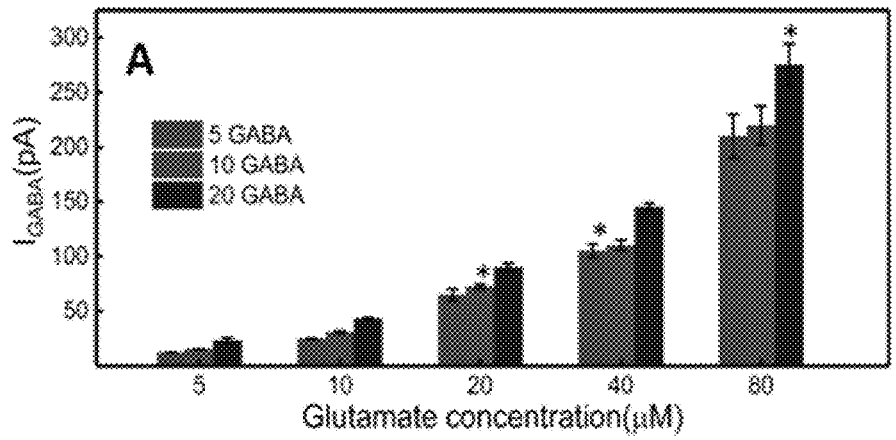
FIGS. 10A to 10C are charts illustrating GABA detection using the GABA and Glu microbiosensors.
Figure 10B:
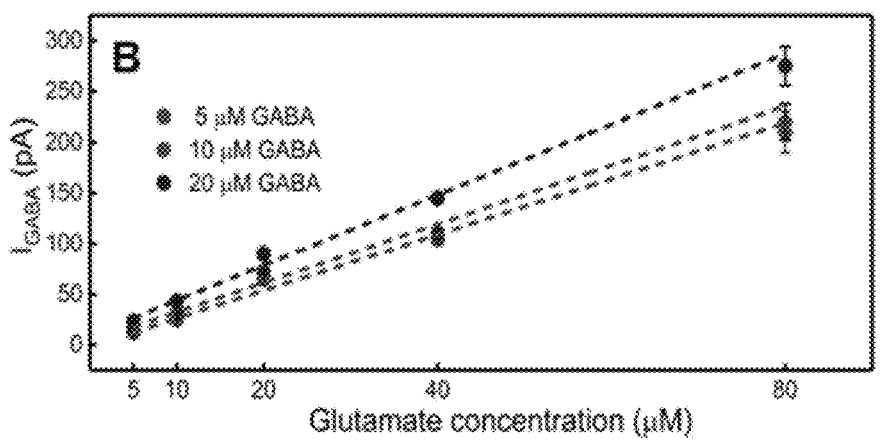
Figure 10C:
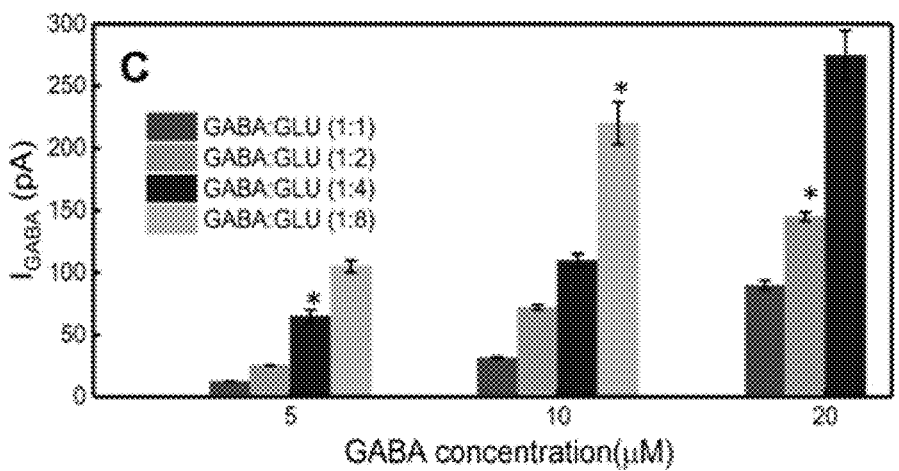

Quantification of GABA using the $I_{GABA}$ and $IH_2O_{2(E)}$ current values Finally, the GABA signal was quantified as $I_{GABA}=IH_2O_{2(site\ 1)}-IH_2O_{2(site\ 2)}$. The $I_{GABA}$ is plotted for varying GABA and Glu concentrations in FIG. 10A after subtracting the Ib noise. The positive values for $I_{GABA}$ at all concentrations of GABA and Glu confirms GABA detection at Site 2. As expected, the $I_{GABA}$ increases as GABA concentrations increase. The GABA calibration curves, following linear approximation of $I_{GABA}$ at various Glu concentrations, is shown in FIG. 10B. A steeper slope is evident at higher GABA concentrations. Values of the slope are 2.7±0.2 pA/μM, 2.9±0.3 pA/μM and 3.5±0.2 pA/μM for 5 μM, 10 μM and 20 μM GABA, respectively. To better understand the GABA signal dependence on Glu concentrations, $I_{GABA}$ values were plotted in terms of different molarity ratios of GABA:Glu (1:1, 1:2, 1:4 and 1:8) for different GABA concentrations (FIG. 10C). It is known that GABA and Glu maintains a certain balance in the human brain by means of the glutamate-glutamine (GABA) cycle (Hertz, 2013) And they exist in a certain molarity ratio based upon the state of the brain. For example, in epilepsy, this cycle becomes imbalanced and Glu levels are elevated (Kanamori and Ross, 2011; Medina-Ceja et al., 2015; Rowley et al., 1995a). The data clearly suggest that the $I_{GABA}$ value is greatly dependent on both GABA and Glu concentration, i.e. the $I_{GABA}$ increases as GABA and Glu levels increases. This is evident from FIG. 10C, which shows that, for a given GABA concentration, the $I_{GABA}$ value is larger for higher GABA:Glu ratios. So, in this approach, for a given $I_{GABA}$ value, the GABA concentration can vary. For example, for a $I_{GABA}$ value of 100 pA, the GABA concentration can be 5 μM, 10 μM or 20 μM. This is because the GABA signal is dependent on the local availability of α-ketoglutarate, which is dependent on the local Glu concentration. Thus, there is no one $I_{GABA}$ value for a given GABA concentration. This problem can be solved by considering the $I_{GABA}$ value from Site 2 and the $IH_2O_{2(E)}$ value from Site 1. From the $IH_2O_{2(E)}$ value, the local Glu concentration can be measured. Once the local Glu concentration is known, (x-coordinate in FIG. 10B), and since the $I_{GABA}$ value is already known (y-coordinate in FIG. 10B), their intersection yields the local GABA concentration. For example, let us say that the $IH_2O_{2(E)}$ value from the Glu microbiosensor is 175 pA and then from FIG. 8B, the Glu concentration will be 50 μM. And, this 50 μM Glu is the x-coordinate in FIG. 10B. Next, let us say that the $I_{GABA}$ value is 175 pA, which is the difference between the $IH_2O_2$ values obtained from the two microbiosensors. Again, the $I_{GABA}$ value is the y-coordinate in FIG. 10B. So, from FIG. 10B, with (x, y) as (50 μM, 175 pA), the intersection of the lines falls on the blue dashed line that corresponds to a GABA concentration of 20 μM.

Finally, in this work, for the in vitro experiments, the microbiosensors were not coated with selective coatings such as nafion and m-phenylenediamine (mPD) that have shown to completely block potential electroactive interferents such as dopamine and ascorbic acid. For the ex vivo testing, the microbiosensors were coated with mPD to achieve selectivity of the probe (Wilson, 2017).

Real-Time Measurement of GABA and Glutamate in Rat Hippocampal Slice Preparation Simultaneous and continuous real-time detection of GABA and glutamate was accomplished using electrically stimulated release in a hippocampal slice model. A range of 100-μA pulse widths was used to induce release of the neurotransmitters (see Table 3) to determine the responsiveness of the sensor to varying levels of stimulation which included single pulses ranging from 1 s to 25-ms in duration and a pulse train of ten 5-ms pulses.

TABLE 3

Stimulation pulse parameters and rise time of the stimulated response.

| Pulse ID | Pulse parameters | Glutamate $t_{r10\text{-}90}$ (s) | Glutamate - GABA $t_{r10\text{-}90}$ (s) | GABA $\Delta t_{r10\text{-}90}$ (s) |
|---|---|---|---|---|
| A | 1000 ms single pulse | 25 ± 2.2 | 17 ± 1.24 | 8 ± 1.2 |
| B | 250 ms single pulse | 19 ± 1.9 | 14 ± 1.1 | 5 ± 0.45 |
| C | 50 ms single pulse | 12 ± 1 | 7 ± 0.85 | 5 ± 0.6 |
| D | Ten 5-ms pulses separated by 1 ms | 12 ± 1 | 7 ± 0.8 | 5 ± 0.75 |
| E | 25 ms single pulse | 7 ± 0.9* | 4 ± 0.25* | 3 ± 0.35* |

Values are expressed in mean ± SEM.
Two-tailed t-test was performed (n = 3, p < 0.05).
*Two-tailed t-test was performed (n = 6, p < 0.05).

The GABA signal was derived by subtracting the signal from the Glu microbiosensor from the GABA microbiosensor. As expected, the amplitude of GABA and glutamate release scaled with pulse width (FIG. 11). In some cases, GABA had a shorter peak duration, and in all cases the concentration of GABA rose faster than glutamate concentration (FIG. 11F). For example, the mean rise time (±SEM) for a 25-ms stimulation was 3.12±0.35 s for GABA and 6.94±0.9 s for glutamate (n=6, p<0.05). Both GABA and glutamate leak out of neuronal synapses after neurons release these neurotransmitters. Mechanisms exist to quickly scavenge and recycle these neurotransmitters, but some molecules diffuse through the extracellular space [Danbolt 2001, Robinson et al., 2016, Boddum et al., 2016]. Thus, there is a slight delay from stimulation to response, as well as a long decay period as GABA and glutamate are eventually cleared. Both of these dynamic processes are evident in the traces shown in FIG. 11 with a rapid, but not immediate increase in neurotransmitter concentration, and a slower decline to baseline representing release and uptake, respectively.

Figure 12A:
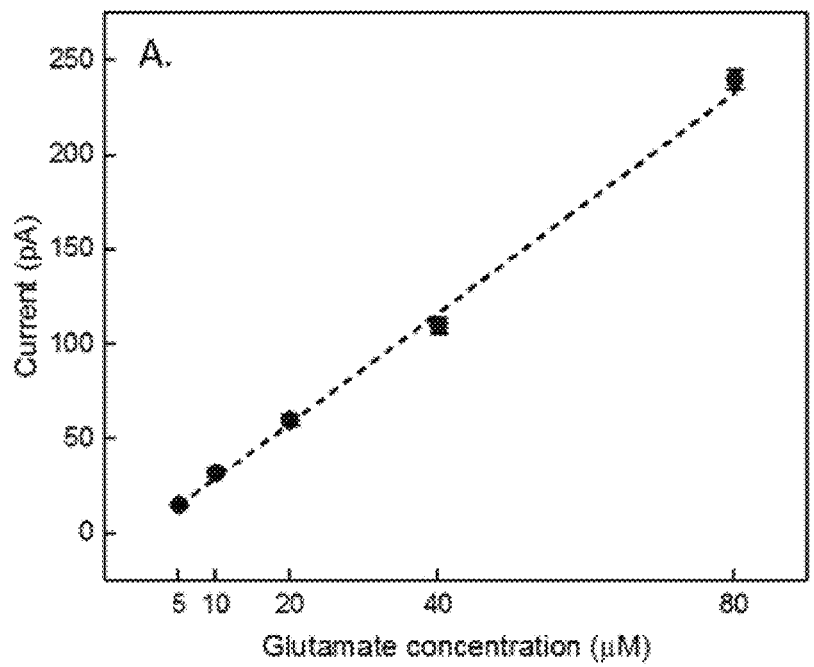
FIGS. 12A and 12B are charts illustrating in vitro current signals for Glu and $I_{GABA}$ taken from the GABA probe.
Figure 12B:
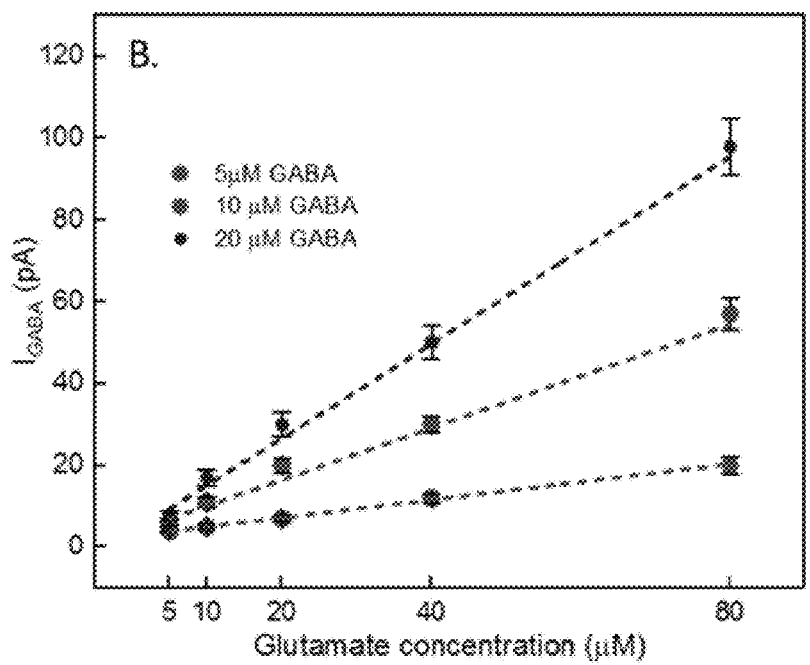

A calibration curve was constructed before performing the ex vivo recordings in order to convert current from GABA release to GABA concentration at the probe (FIG. 12A). This calibration curve is constructed based on the procedure detailed in FIG. 8B. The data plotted in FIG. 12B is constructed in the same way as that of FIG. 10B. Peak current measurements in Table 4 represent a range of stimulated release of GABA and glutamate.

TABLE 4

Conversion of current to glutamate and GABA concentration in ex vivo recordings.

| Points[1] | Glutamate Signal (pA)[2] | Glutamate (μM)[3] | Difference in signal (pA)[4] | GABA (μM)[5] |
|---|---|---|---|---|
| 1 | 74 | 35 | 25 | 13 |
| 2 | 10 | 5 | 6 | 5 |

[1]Number corresponds to signal trace number in FIG. 7A.
[2]From FIG. 7E, the $IH_2O_2(E)$ value, i.e. the local Glu signal is measured.
[3]Then the local Glu concentration is known from FIG. 8A.
[4]The $I_{GABA}$ value is the difference between the $IH_2O_2$ values obtained from the two microbiosensors.
[5]Now, knowing the Glu concentration, which is the x-coordinate in FIG. 8B and the $I_{GABA}$ value, which is the y-coordinate in FIG. 8B, one can find the GABA concentration for the two points.

These measurements correspond to curves labeled 1-2 in FIG. 11A. Peak concentrations ranged from 5-35 μM for glutamate and 5-13 μM for GABA. Thus, these probes can measure GABA and glutamate at concentrations that are well below normal levels (Grabauskas, 2004, Moussawi et al., 2011) making them suitable to study impaired release in disease states. Furthermore, numerous cycles of stimulated release with consistent current amplitude for each level of stimulation and without adding any exogenous substrates, such as α-ketoglutarate, support the premise that endogenous products of the conversion of glutamate provide the substrate for the GABASE reaction. This is an important capability for future in vivo applications.

In the foregoing disclosure, a novel GABA microarray probe is described that can detect GABA without the addition of any external reagents such as α-ketoglutarate and NADPH in vitro. The GABA probe includes two microbiosensors that were modified with GOx and GOx+GABASE enzymes. By simultaneously measuring and subtracting the oxidation currents of $H_2O_2$ generated from the microbiosensors. GABA was detected with a sensitivity of 36±2.5 pA $\mu M^{-1}$ $cm^{-2}$ and LOD of 2±0.12 µM. A new detection method was demonstrated that will assist neuroscientists to better understand the combined role of GABA (a major inhibitory neurochemical) and Glu (a major excitatory neurochemical) in real-time in the brain. Benefits of the proposed approach include: (1) the probe can be easily multiplexed to simultaneously measure other important neurochemicals, which is not possible with other commonly used electrodes for chemical sensing, (2) ability to detect GABA in real time without adding reagents (i.e. truly self-contained), (3) it can be constructed on an established, commercially available Pt MEA platform that is suitable for future in vivo recordings, (4) the location of the MEAs along the long shank allows GABA and Glu sensing at multiple depths in the brain, and (5) it can simultaneously sense neurochemicals and field potentials for multimodal (e.g. neurochemical and neuroelectrical) recordings, which is not possible with the current neurochemical technologies. Furthermore, it was demonstrated the utility of the microbiosensor microarray to simultaneously record fluctuations in electrically stimulated GABA and glutamate release continually and in real time in a rat hippocampal slice preparation. Moreover, GABA release can be detected over repeated stimulations without adding substrate compounds externally.

REFERENCES

Arima, J., Sasaki, C., Sakaguchi, C., Mizuno, H., Tamura, T., Kashima, A., et al. (2009). Structural characterization of l-glutamate oxidase from *Streptomyces* sp. X-119-6. FEBS J. 276, 3894-3903. doi:10.1111/j.1742-4658.2009.07103.x.

Artavazd Badalyan, Silke Leimkühler, Konstanze Stiba, U. W. (2007). Biosensor for measuring GABA. EP 2505658 A1 1, 1-18. doi:10.1371/journal.pone.0010853.

Auteri, M., Zizzo, M. G., and Serio, R. (2015). The GABAergic System and the Gastrointestinal Physiopathology. Curr. Pharm. Des. 21, 4996-5016. doi: 10.2174/1381612821666150914121518

Badalyan, A., Dierich, M., Stiba, K., Schwuchow, V., Leimkuhler, S., and Wollenberger, U. (2014). Electrical wiring of the aldehyde oxidoreductase PaoABC with a polymer containing osmium redox centers: Biosensors for benzaldehyde and GABA. Biosensors 4, 403-421. doi: 10.3390/bios4040403.

Bhat, R., Axtell, R., Mitra, A., Miranda, M., Lock, C., Tsien, R. W., et al. (2010). Inhibitory role for GABA in autoimmune inflammation. Proc. Natl. Acad. Sci. 107, 2580-2585. doi:10.1073/pnas.0915139107.

Boddum K, Jensen T P, Magloire V, Kristiansen U, Rusakov D A, Pavlov I, Walker M C. Astrocytic GABA transporter activity modulates excitatory neurotransmission. Nature Communications, 2016 Nov. 25; 7:13572. doi: 10.1038/ncomms13572.

Burmeister, J. J., Davis, V. A., Quintero, J. E., Pomerleau, F., Huettl, P., and Gerhardt, G. A. (2013). Glutaraldehyde cross-linked glutamate oxidase coated microelectrode arrays: Selectivity and resting levels of glutamate in the CNS. ACS Chem. Neurosci. 4, 721-728. doi:10.1021/cn4000555.

Caudill, W. L., Houck, G. P., and Wightman, R. M. (1982). Determination of gamma-aminobutyric acid by liquid chromatography with electrochemical detection. J. Chromatogr. 227, 331-9. doi:10.1016/50378-4347(00)80387-4.

Cifuentes Castro, V. H., López Valenzuela, C. L., Salazar Sánchez, J. C., Peña, K. P., López Pérez, S. J., Ibarra, J. O., et al. (2014). An update of the classical and novel methods used for measuring fast neurotransmitters during normal and brain altered function. Curr. Neuropharmacol. 12, 490-508. doi:10.2174/1570159X13666141223223657.

Danbolt, N. C., 2001. Glutamate uptake. Prog. Neurobiol. 65, 1-105. https://doi.org/10.1016/S0301-0082(00)00067-8.

Garguilo, M. G., and Michael, A. C. (1994). Quantitation of Choline in the Extracellular Fluid of Brain Tissue with Amperometric Microsensors. Anal. Chem. 66, 2621-2629. doi:10.1021/ac00089a006.

Grabauskas, G. (2004). Time course of GABA in the synaptic clefts of inhibitory synapses in the rostral nucleus of the solitary tract. Neurosci. Lett. 373, 10-15. doi:10.1016/j.neulet.2004.09.051.

Hascup, K. N., Rutherford, E. C., Quintero, J. E., Day, B. K., Nickell, J. R., Pomerleau, F., et al. (2007). "Second-by-Second Measures of L-Glutamate and Other Neurotransmitters Using Enzyme-Based Microelectrode Arrays" in Electrochemical Methods for Neuroscience, ed. A. C. Micheal and L. M. Borland (Boca Raton, FL: CRC Press/Taylor & Francis), 407-450.

Hertz, L. (2013). The Glutamate-Glutamine (GABA) Cycle: Importance of Late Postnatal Development and Potential Reciprocal Interactions between Biosynthesis and Degradation. Front. Endocrinol. (Lausanne). 4:59. doi: 10.3389/fendo.2013.00059.

Kanamori, K., and Ross, B. D. (2011). Chronic electrographic seizure reduces glutamine and elevates glutamate in the extracellular fluid of rat brain. Brain Res. 1371, 180-191. doi:10.1016/j.brainres.2010.11.064.

Ke, Y., Cohen, B. M., Bang, J. Y., Yang, M., and Renshaw, P. F. (2000). Assessment of GABA concentration in human brain using two-dimensional proton magnetic resonance spectroscopy. Psychiatry Res. 100, 169-78. doi: 10.1016/S0925-4927(00)00075-5

Kehr, J., and Ungerstedt, U. (1988). Fast HPLC estimation of gamma-aminobutyric acid in microdialysis perfusates: effect of nipecotic and 3-mercaptopropionic acids. J. Neurochem. 51, 1308-10. doi:org/10.1111/j.1471-4159.1988.tb03101.x Khan, R., Gorski, W., and Garcia, C. D. (2011). Nanomolar Detection of Glutamate at a Biosensor Based on Screen-Printed Electrodes Modified with Carbon Nanotubes. Electroanalysis 23, 2357-2363. doi:10.1002/elan.201100348.

Long, L. H., and Halliwell, B. (2011). Artefacts in cell culture: α-Ketoglutarate can scavenge hydrogen peroxide generated by ascorbate and epigallocatechin gallate in cell culture media. Biochem. Biophys. Res. Commun. 406, 20-24. doi:10.1016/J.BBRC.2011.01.091.

Mazzei, F., Botrè, F., Lorenti, G., and Porcelli, F. (1996). Peroxidase based amperometric biosensors for the determination of γ-aminobutyric acid. Anal. Chim. Acta 328, 41-46. doi:10.1016/0003-2670(96)00089-X.

Medina-Ceja, L., Pardo-Peña, K., Morales-Villagrín, A., Ortega-Ibarra, J., and López-Pérez, S. (2015). Increase in the extracellular glutamate level during seizures and electrical stimulation determined using a high temporal resolution technique. BMC Neurosci. 16:11. doi:10.1186/s12868-015-0147-5.

Monge-Acuña, A. A., and Fornaguera-Trías, J. (2009). A high performance liquid chromatography method with electrochemical detection of gamma-aminobutyric acid, glutamate and glutamine in rat brain homogenates. J. Neurosci. Methods 183, 176-181. doi:10.1016/j.jneumeth.2009.06.042.

Moussawi, K., Riegel, A., Nair, S., and Kalivas, P. W. (2011). Extracellular glutamate: functional compartments operate in different concentration ranges. Front. Syst. Neurosci. 5:94. doi:10.3389/fnsys.2011.00094.

Nath, K. A., Ngo, E. O., Hebbel, R. P., Croatt, A. J., Zhou, B., and Nutter, L. M. (1995). alpha-Ketoacids scavenge $H_2O_2$ in vitro and in vivo and reduce menadione-induced DNA injury and cytotoxicity. Am. J. Physiol. 268, C227-36. doi:10.1152/ajpcell.1995.268.1.C227.

Niwa, O., Kurita, R., Horiuchi, T., and Torimitsu, K. (1998). Small-volume on-line sensor for continuous measurement of gamma-aminobutyric acid. Anal. Chem. 70, 89-93. doi:10.1021/ac970740z.

Paula S. Cahill, Q. David Walker, Jennifer M. Finnegan, George E. Mickelson, Eric R. Travis, and, and Wightman, R. M. (1996). Microelectrodes for the Measurement of Catecholamines in Biological Systems. Anal. Chem., 1996, 68 (18), pp 3180-3186 doi:10.1021/AC960347D.

Reinhoud, N. J., Brouwer, H. J., Van Heerwaarden, L. M., and Korte-Bouws, G. A. H. (2013). Analysis of glutamate, GABA, noradrenaline, dopamine, serotonin, and metabolites using microbore UHPLC with electrochemical detection. ACS Chem. Neurosci. 4, 888-894. doi:10.1021/cn400044s.

Robinson, D. L., Hermans, A., Seipel, A. T., and Wightman, R. M. (2008). Monitoring rapid chemical communication in the brain. Chem. Rev. 108, 2554-84. doi:10.1021/cr068081q.

Robinson, D. L., and Wightman, R. M. (2007) "Rapid Dopamine Release in Freely Moving Rats" in Electrochemical Methods for Neuroscience, ed. A. C. Micheal and L. M. Borland (Boca Raton, FL: CRC Press/Taylor & Francis), 17-34.

Robinson, M. B., Jackson, J. G., 2016. Astroglial glutamate transporters coordinate excitatory signaling and brain energetics. Neurochem. Int. 98, 56-71. https://doi.org/10.1016/j.neuint.2016.03.014.

Rowley, H. L., Martin, K. F., and Marsden, C. A. (1995a). Decreased GABA release following tonic-clonic seizures is associated with an increase in extracellular glutamate in rat hippocampus in vivo. Neuroscience 68, 415-22. doi:10.1016/0306-4522(95)00159-G Rowley, H. L., Martin, K. F., and Marsden, C. A. (1995b). Determination of in vivo amino acid neurotransmitters by high-performance liquid chromatography with o-phthalaldehyde-sulphite derivatisation. J. Neurosci. Methods 57, 93-99. doi:10.1016/0165-0270(94)00132-Z.

Sandberg, S. G., and Garris, P. A. (2010). "Neurochemistry of Addiction: Monitoring Essential Neurotransmitters of Addiction" in Advances in the Neuroscience of Addiction. 2nd edition ed. CM Kuhn and GF Koob. (Boca Raton, FL: CRC Press/Taylor & Francis), 120-169.

Sekioka, N., Kato, D., Kurita, R., Hirono, S., and Niwa, O. (2008). Improved detection limit for an electrochemical γ-aminobutyric acid sensor based on stable NADPH detection using an electron cyclotron resonance sputtered carbon film electrode. Sensors Actuators, B Chem. 129, 442-449. doi:10.1016/j.snb.2007.08.040.

Sethi, M. L. (1993). Enzyme inhibition X: colorimetric method for determining gabase activity and its comparison with a spectrophotometric method. J. Pharm. Biomed. Anal. 11, 613-7. doi:org/10.1016/0731-7085(93)80013-Q.

Smith, S., and Sharp, T. (1994). Measurement of GABA in rat brain microdialysates using o-phthaldialdehyde-sulphite derivatization and high-performance liquid chromatography with electrochemical detection. J. Chromatogr. B Biomed. Sci. Appl. 652, 228-233. doi:10.1016/0378-4347(93)E0391-3.

Song C Z, TA Murray, R Kimura, M Wakui, K Ellsworth, K M Schroeder, S Marxer-Miller, R J Lukas, and J Wu (2005) Role of α7-nicotinic acetylcholine receptors in tetanic stimulation-induced γ oscillations in rat hippocampal slices. Neuropharmacology 48 (6): 869-880, http://www.sciencedirect.com/science/article/pii/S002839080500033X Tian, J., Lu, Y., Zhang, H., Chau, C. H., Dang, H. N., and Kaufman, D. L. (2004). Gamma-aminobutyric acid inhibits T cell autoimmunity and the development of inflammatory responses in a mouse type 1 diabetes model. J. Immunol. 173, 5298-304 doi:org/10.4049/jimmunol.173.8.5298

Ting Wong, C. G., Bottiglieri, T., and Snead, O. C. (2003). GABA, γ-hydroxybutyric acid, and neurological disease. Ann. Neurol. 54, S3-S12. doi:10.1002/ana.10696.

Tretter, L., and Adam-Vizi, V. (2005). Alpha-ketoglutarate dehydrogenase: a target and generator of oxidative stress. Philos. Trans. R. Soc. Lond. B. Biol. Sci. 360, 2335-45. doi:10.1098/rstb.2005.1764.

Tseng, T., Chang, C.-F., and Chan, W.-C. (2014). Fabrication of Implantable, Enzyme-Immobilized Glutamate Sensors for the Monitoring of Glutamate Concentration Changes in Vitro and in Vivo. Molecules 19, 7341-7355. doi:10.3390/molecules19067341.

Willuhn, I., Wanat, M. J., Clark, J. J., and Phillips, P. E. M. (2010). Dopamine Signaling in the Nucleus Accumbens of Animals Self-Administering Drugs of Abuse. Curr. Top. Behave. Neurosci., 3, 29-71. doi:10.1007/7854_2009_27.

Wilson, L. R., Panda, S., Schmidt, A. C., and Sombers, L. A. (2017). Selective and Mechanically Robust Sensors for Electrochemical Measurements of Real-Time Hydrogen Peroxide Dynamics In Vivo. doi:10.1021/acs.analchem.7b03770.

The invention claimed is:

1. A GABA detecting probe comprising:
(a) a probe body;
(b) a Glu micro-sensor located on the probe body, the Glu micro-sensor including at least one Pt electrode having a surface modification with GOx and a binding matrix;
(c) a GABA micro-sensor located on the probe body, the GABA micro-sensor including at least one Pt electrode having a surface modification with GABASE, GOx, and the binding matrix, the GABA and Glu micro-sensors being positioned no further than 250 um apart on the probe body;

(d) a sentinel site located on the probe body, the sentinel site including at least one Pt electrode having a surface modification with the binding matrix, but no GOx or GABASE; and (e) wherein the Pt electrodes each include (i) a surface area of less than 35,000 um$^2$, and (ii) a connecting lead attached thereto and extending along the probe body.

2. The GABA detecting probe according to claim 1, wherein the binding matrix includes bovine serum albumin and glutaraldehyde.

3. The GABA detecting probe according to claim 1, wherein the probe body is formed by a plurality of insulated microwires bound together and wherein (i) the uninsulated end of a first microwire forms the Glu micro-sensor, and (ii) the uninsulated end of a second microwire forms the GABA micro-sensor.

4. The GABA detecting probe according to claim 3, wherein the uninsulated end of a third microwire forms the sentinel site.

5. The GABA detecting probe according to claim 1, wherein the sentinel site has no enzyme formed on the binding matrix.

6. The GABA detecting probe according to claim 1, wherein the probe body has at least one additional pair of GABA and Glu micro-sensors.

7. The GABA detecting probe according to claim 1, wherein a reference electrode is positioned relative to the probe body in order to form an electrochemical cell in relation to the other electrodes.

8. The GABA detecting probe according to claim 6, wherein the reference electrode is an Ag/AgCl electrode.

9. The GABA detecting probe according to claim 1, wherein the Pt electrodes' surface area coated with an enzyme is between 1000 and 20,000 um$^2$.

10. The GABA detecting probe according to claim 1, wherein the Pt electrodes having GOx or GABASE formed thereon have at least 0.02 units of activity of enzymes on the electrodes.

11. The GABA detecting probe according to claim 1, wherein the sentinel site is positioned within 250 um the GABA and Glu micro-sensors.

12. The GABA detecting probe according to claim 1, wherein (i) the probe is an elongated section of rigid non-conducting or semi-conducting material less than 5 mm in width and 15 mm in length, and (ii) the micro-sensors are formed on the non-conducting material.

13. A method of detecting GABA in a brain cell mass comprising the steps of:

(a) inserting a probe body into the brain cell mass, the probe comprising:

(i) a Glu micro-sensor located on the probe body, the Glu micro-sensor including at least one Pt electrode having a surface modification with GOx and a binding matrix;

(ii) a GABA micro-sensor located on the probe body, the GABA micro-sensor including at least one Pt electrode having a surface modification with GABASE, GOx, and the binding matrix, the GABA and Glu micro-sensors being positioned no further than 250 um apart on the probe body;

(iii) a sentinel site located on the probe body, the sentinel site including at least one Pt electrode having the binding matrix but no GOx or GABASE; and (iv) wherein the Pt electrodes each include (1) a surface area of less than 35,000 um2, and (2) a connecting lead attached thereto and extending along the probe body;

(b) receiving at a potentiostat electrical signals from the connecting leads and determining an electro-potential difference between the GABA micro-sensor and Glu micro-sensor.

14. The method of claim 13, wherein the brain cell mass is one of (i) a culture of mammal brain cells, (ii) a tissue slice of a mammal brain, or (iii) a mammal brain in an in vivo application.

15. The method of claim 13, further comprising placement of a reference electrode and maintaining a potential of between 0.6 and 0.8 volts between the reference electrode and the micro-sensors and the sentinel site.

16. The method of claim 13, further comprising the step placing a cannula into a mammal brain and inserting the probe through the cannula into contact with brain tissue.

17. A method of manufacturing a GABA probe comprising the steps of:

(a) providing a probe body;

(b) forming a Glu micro-sensor on the probe body, the Glu micro-sensor including at least one Pt electrode having a surface modification with GOx and a binding matrix;

(c) forming a GABA micro-sensor on the probe body, the GABA micro-sensor including at least one Pt electrode having a surface modification with GABASE, GOx, and the binding matrix, the GABA and Glu micro-sensors being positioned no further than 250 um apart on the probe body;

(d) forming a sentinel site on the probe body, the sentinel site including at least one Pt electrode having the binding matrix but no GOx or GABASE; and (e) wherein the Pt electrodes each include (i) a surface area of less than 35,000 um$^2$, and (ii) a connecting lead is attached thereto and extends along the probe body.

18. The method of claim 17, wherein the step of providing a probe body includes binding together a plurality of microwires.

19. The method of claim 18, further comprising the step of forming the Glu micro-sensor on an end of a first microwire and forming the GABA micro-sensor on a second microwire.

20. The method of claim 18, further comprising the step of forming the sentinel site on an end of a third microwire.

* * * * *